United States Patent
Kato

(10) Patent No.: US 7,399,283 B2
(45) Date of Patent: Jul. 15, 2008

(54) MEDICAL GUIDE WIRE HAVING A STEPWISELY THICKNESS-REDUCED BUT BREADTH-INCREASED DISTAL TIP STRUCTURE

(75) Inventor: Tomihisa Kato, Aichi-ken (JP)

(73) Assignee: Asahi Intecc Co., Nagoya-shi, Aichi-ken (JP)

( * ) Notice: Subject to any disclaimer, the term of this patent is extended or adjusted under 35 U.S.C. 154(b) by 61 days.

(21) Appl. No.: 10/950,683

(22) Filed: Sep. 28, 2004

(65) Prior Publication Data
US 2005/0096568 A1    May 5, 2005

(30) Foreign Application Priority Data
Oct. 2, 2003    (JP)    ............... 2003-343901

(51) Int. Cl.
*A61B 5/00*    (2006.01)
*A61M 25/00*    (2006.01)

(52) U.S. Cl. .................................................. 600/585
(58) Field of Classification Search ................ 600/585, 600/433–435
See application file for complete search history.

(56) References Cited

U.S. PATENT DOCUMENTS

| | | | |
|---|---|---|---|
| 5,365,942 A | | 11/1994 | Shank |
| 5,520,194 A | * | 5/1996 | Miyata et al. ............... 600/585 |
| 5,720,300 A | * | 2/1998 | Fagan et al. ............... 600/585 |
| 5,788,654 A | * | 8/1998 | Schwager ................... 600/585 |
| 5,910,364 A | | 6/1999 | Miyata et al. |
| 5,916,166 A | * | 6/1999 | Reiss et al. ................. 600/434 |
| 5,957,865 A | | 9/1999 | Backman et al. |
| 6,165,140 A | * | 12/2000 | Ferrera ....................... 600/585 |
| 6,325,766 B1 | * | 12/2001 | Anderson et al. ........... 600/585 |
| 6,491,648 B1 | | 12/2002 | Cornish et al. |
| 2003/0181828 A1 | | 9/2003 | Fujimoto et al. |
| 2006/0089568 A1 | * | 4/2006 | Nuss .......................... 600/585 |

FOREIGN PATENT DOCUMENTS

| | | |
|---|---|---|
| EP | 0 495 299 A1 | 7/1992 |
| JP | 4-292175 | 10/1992 |
| JP | 2002-272854 | 9/2002 |
| JP | 2003-299738 | 10/2003 |

* cited by examiner

*Primary Examiner*—Max F. Hindenburg
*Assistant Examiner*—Michael Apanius
(74) *Attorney, Agent, or Firm*—Morgan, Lewis & Bockius LLP

(57) ABSTRACT

In a medical guide wire, a core line securement portion (11) is provided in which the core wire (2) is fixed to an inner side of the helical coil body (3) so as to form a top leading end portion (10) between the core line securement (11) and the head plug (4). A flat plane structure (13) is formed in which the core wire (2) of the top leading end portion (10) gradually changes through stepped portions (S) so that the core wire (2) progressively reduces its thickness stepwisely while successively increasing its breadth stepwisely as approaching a foremost distal end of the top leading end portion (10). This provides an improved flexibility, sensitivity, torsibility and torque transmissibility with the flat plane structure (13) so as to be accessible to the diseased area with a high detective and ablative ability.

10 Claims, 8 Drawing Sheets

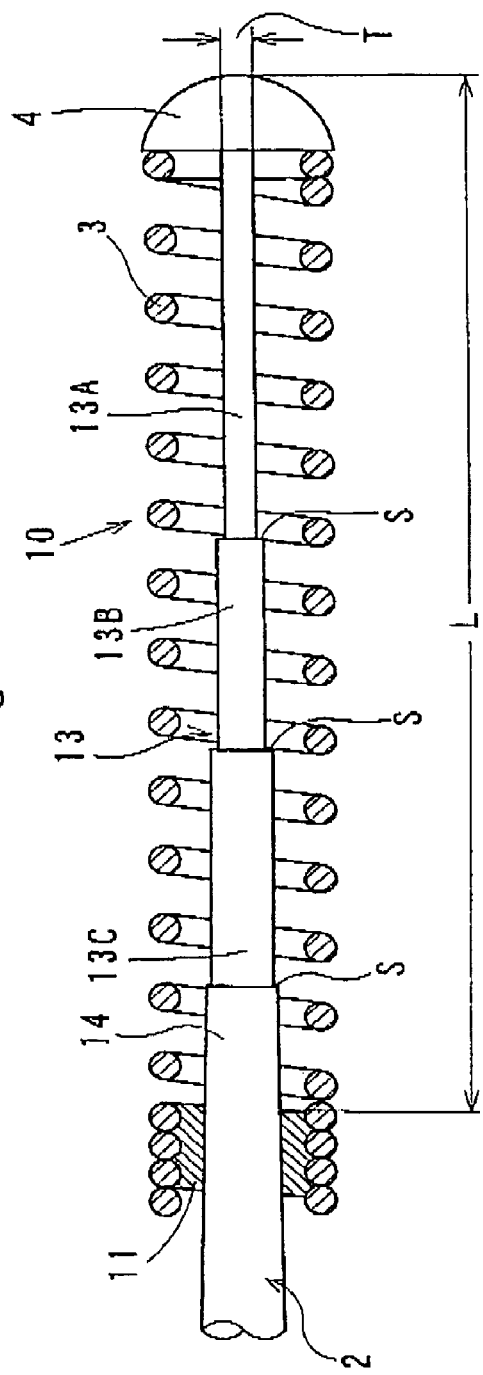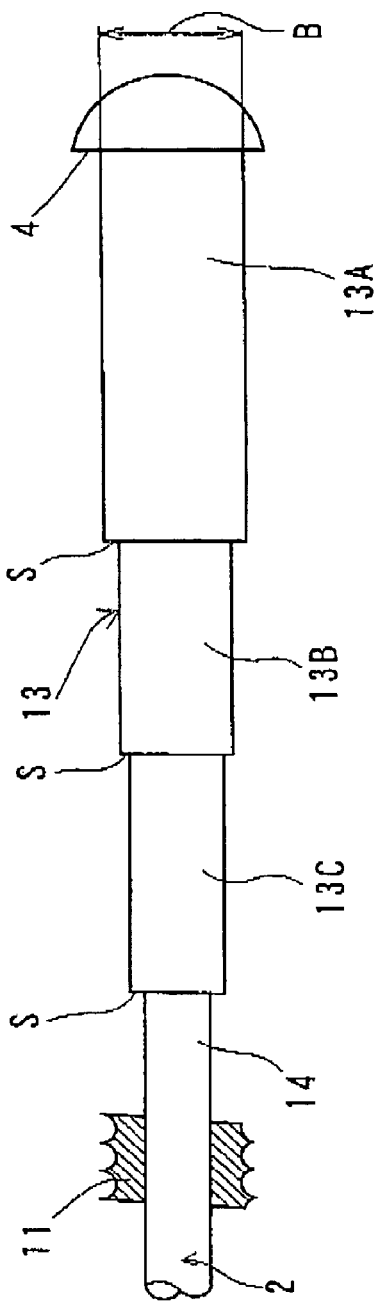

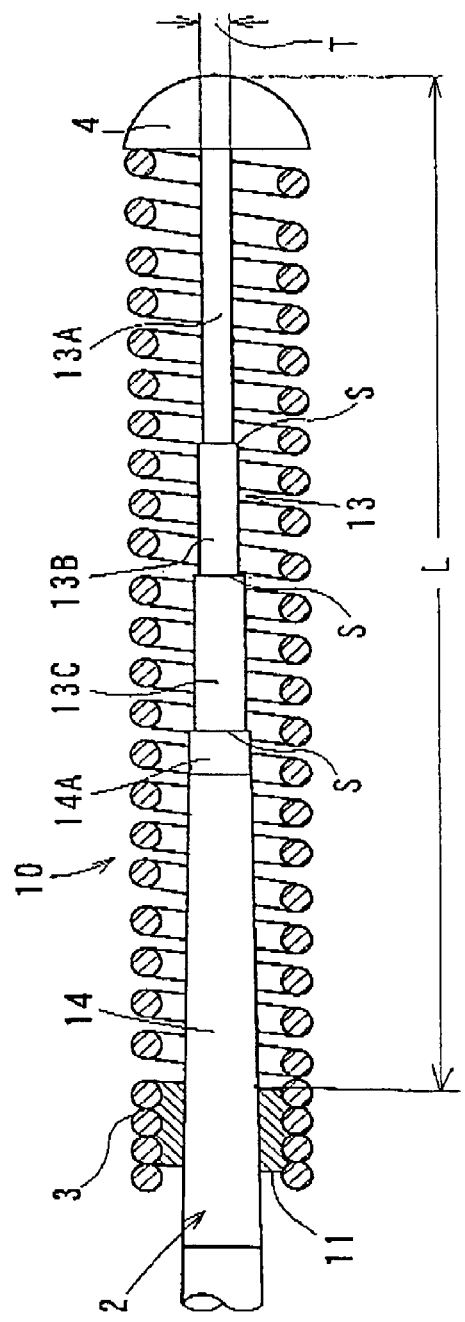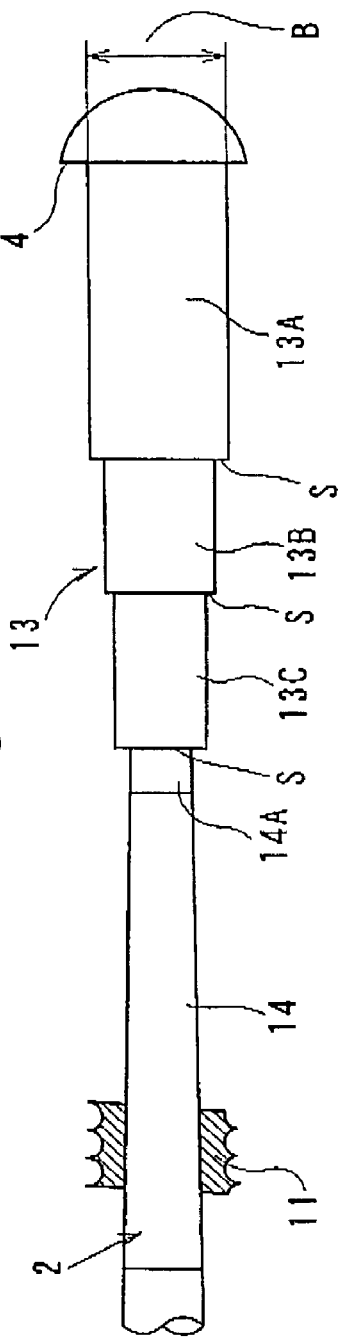

Intrahepatic Artery Segments

MEDICAL GUIDE WIRE HAVING A STEPWISELY THICKNESS-REDUCED BUT BREADTH-INCREASED DISTAL TIP STRUCTURE

BACKGROUND OF TIME INVENTION

1. Field of the Invention

The invention relates to a medical guide wire to facilitate inserting a catheter into a cardiovascular system and hepatovascular system, and particularly concerns a medical guide wire with an improved leading distal end structure.

2. Description of Related Art

A medical guide wire has been used to assist a very thin and flexible catheter to insert it into a blood vessel, to check its diseased area with an angiography to facilitate using a balloon catheter to treat a coronary stenosis, and to insert the catheter into a hepatovascular system to cure a diseased area of the liver.

In these applications, the leading distal end of the medical guide wire is introduced into the diseased area through a sinuous vascular system, a bifurcated blood vessel or a vascular stenosis by a "push-pull and turn" manipulation at a hand access portion located outside a subject patient.

To achieve a smooth manipulation when inserting the leading distal end into the diseased area, the medical guide wire must have multi-mechanical properties. The multi-mechanical properties include high flexibility, good torque transmissibility and high bending characteristics with a small radius of curvature together with a good steerability by the hand access portion.

By way of illustration, FIG. 12 shows a diseased area (P) in which a completely obstructed area 25 occurs in a blood vessel (T) consisting of the intima 21, the media 22 and the adventitia. The completely obstructed area 25 is 10-15 mm long and filled with occlusive substances such as atheroma, plaque, thrombi. Both ends of the obstructed area 25 are calcified with a deposit of calcium salt to form a hardened fibrous cap.

In this example, a user steers a leading distal end 106 of a guide wire (G) at the obstructed area 25 to feel for a reaction against a concave area of the vascular wall based on a sensation coming to the hand access portion. Then, the user moves the guide wire (G) to a normal position (GA) by repeatedly pushing and turning the leading distal end 106 within a range of 2-3 mm. In order to efficiently and precisely perform the manipulation, it is necessary to give the guide wire (G) a high flexibility, a good torque transmissibility and sensitivity against the vascular wall. When the leading distal end 106 of the guide wire (G) lacks the flexibility, the leading distal end 106 does not follow a curved profile at the sinuous blood vessel. The leading distal end 106 is prone to remaining straight and likely advances into the intima 21 and the media 22 so as to often result in a vascular perforation as shown in FIG. 13. Otherwise, the leading distal end 106 unfavorably induces a false lumen 26 as shown in FIG. 14. In order to avoid these problems, it is necessary for the leading distal end 106 to have a bending characteristics that allow it to bend at an extremely small radius of curvature.

A medical guide wire with some of these mechanical properties has been introduced in a Laid-open Japanese Patent Application No. 4-292175. In this prior art reference, a flexible and elongated shaft portion 100 is disclosed as a main portion with its rear portion manipulated by a hand access portion 107 as shown in FIG. 15. A front distal end portion of the shaft portion 100 has a thin core wire 102 which is inserted into a helical coil body. A head plug 104 is secured to both top distal front end of the core wire 102 and the helical coil body 103 so as to form the leading distal end 106. As shown in FIGS. 16 and 17, the leading distal end 106 has a core line securement portion 111 somewhat remote (e.g., approximately 26 mm) from the front distal end of the head plug 104 to secure the helical coil body 103 to the core wire 102 by means of a soldering procedure. A lengthwise extension of the core wire 102 from the core line securement portion 111 to a proximal end of the head plug 104, progressively increases its breadth (m) variably toward the front distal end of the head plug 104 while successively reducing its thickness (h) variably to taper off toward the front distal end of the head plug 104 so as to form a duckbill structure 130.

The leading distal end 106 of the duckbill structure 130 has as its objective merely to allow a selective insertability against the bifurcated portion of the blood vessel, and accordingly, diminishing detection of the stenosis and the obstructed area of the blood vessel, thus reducing an ablative ability against a narrow portion of the blood vessel and lowering the sensitivity against the vascular wall and the diseased area.

Therefore, it is an objective of the invention to overcome the above drawbacks by improving the indispensable mechanical properties so as to provide a high quality medical guide wire with good performance.

SUMMARY OF THE INVENTION

According to the present invention, there is provided a medical guide wire in which a core wire is inserted into a helical coil body, and a head plug is attached to each distal end of the core wire and the helical coil body so as form a flexible and linear front distal end portion.

A core line securement portion is provided in which the core wire is fixed to an inner side of the helical coil body so as to form a top leading end portion between the core line securement and the head plug. A flat plane structure is formed in which the core wire of the top leading end portion gradually changes through stepped portions so that the core wire progressively reduces its thickness stepwisely while successively increasing its breadth stepwisely as it approaches a foremost distal end of the top leading end portion. A cross sectional area of the core wire of each of the flat plane structures is equal throughout its lengthwise direction.

The flat plane structure is such that the helical coil body and the core wire are subjected to a bending, twisting and turning operation by manipulating the hand access portion. The stepped portions are provided with the core wire as stress concentration points in which the stepped portions dominate the flexibility, the torsility, the torque transmissibility and the tactility in the flat plane structure. Due to the gradually changing structure in which the top leading end portion is formed to be thinner and wider stepwisely toward its distal end portion with the stepped portions as nodal points, improved mechanical properties are provided with the top leading end portion of the flat plane structure.

In more tangible terms, the core wire of the top leading end portion has a core wire portion circular in cross section or tapered off toward its foremost distal end portion, and having the flat plane structure contiguous with the core wire portion. Two or three stepped portions are formed across the core wire.

Furthermore, in order to adequately adapt the top leading end portion to the diseased area, the top leading end portion has a length of 24-45 mm measured from the foremost distal end of the head plug to the core line securement portion. In another form, the core wire is of stranded wires, and wrought to reduce its outer diameter by means of e.g., a swaging procedure. Alternatively, the core wire is made of an austenitic stainless steel.

Such is the top leading end portion that the core wire is formed to be thinner and wider stepwise toward its distal end portion with the stepped portions as nodal points in the flat plane structure. The core wire dominates the bending characteristics of the top leading end portion when the top leading end portion is subjected to a torsional force (rotational force) upon manipulating the hand access portion or when subjected to a bending force as an reaction upon inserting it into the blood vessel. For this reason, the stepped portions are subjected to concentrated stresses with segment plates as bending sections due to the torsional and bending displacements.

The segment plates divided by the nodal points are subjected to the bending and torsional forces at once depending on a flattened degree of the respective segment plates so as to make the resultant force work on the top leading end portion as a whole. Due to the resultant force, the segment plate between the first stepped portion and the foremost distal end of the core wire serves as a short tongue piece conducive to providing it with a good flexibility and tactility due to a sensitivity against the vascular wall and the diseased area.

BRIEF DESCRIPTION OF THE DRAWINGS

Preferred forms of the present invention are illustrated in the accompanying drawings in which:

FIG. 6 is a longitudinal cross sectional view of a medical guide wire according to a second embodiment of the invention, but only a top leading end portion is shown;

FIG. 7 is a plan view of the medical guide wire, but only a top leading end portion is shown with a helical coil body removed;

FIG. 8 is a longitudinal cross sectional view of a medical guide wire according to a third embodiment of the invention, but only a top leading end portion is shown;

FIG. 9 is a plan view of the medical guide wire, but only a top leading end portion is shown with a helical coil body removed;

DETAILED DESCRIPTION OF THE PREFERRED EMBODIMENTS

Figure 1:
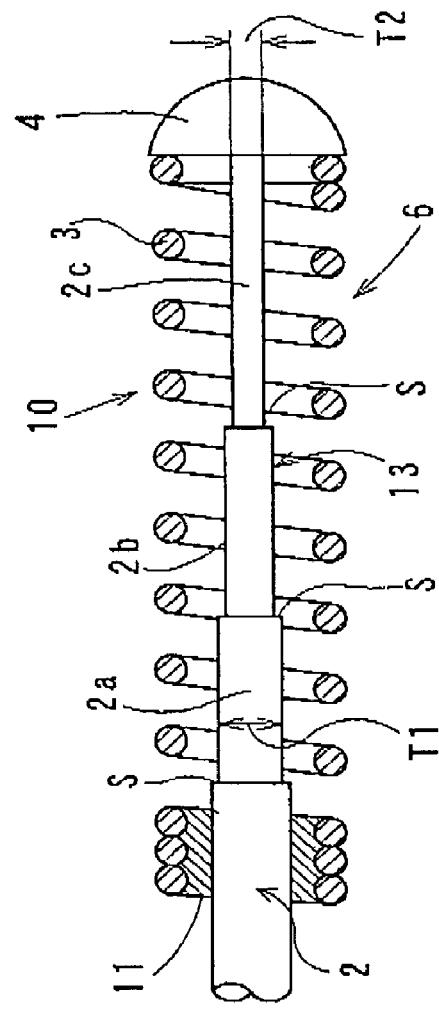
FIG. 1 is a longitudinal cross sectional view of a medical guide wire according to a first embodiment of the invention, but only a top leading end portion is shown.
Figure 2:
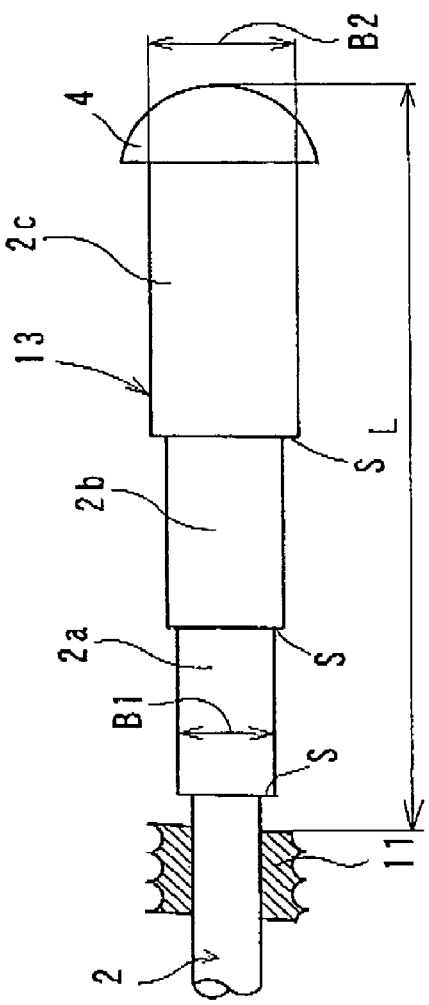
FIG. 2 is a plan view of the medical guide wire, but only a top leading end portion is shown with a helical coil body removed.

In the following description of the depicted embodiments, the same reference numerals are used for features of the same type. Referring to FIGS. 1 and 2, a medical guide wire (abbreviated as "guide wire" hereinafter) according to a first embodiment of the invention is described below.

A front distal end structure of the guide wire has a core wire 2 inserted into a helical coil body 3, and having a head plug 4 attached to each distal end of the core wire 2 and the helical coil body 3 so as form a flexible and linear front distal end portion 6. A core line securement portion 11 is provided in which the core wire 2 is fixed to an inner side of the helical coil body 3 so as to form a top leading end portion 10 between the core line securement 11 and the head plug 4. A flat plane structure 13 is formed in which the core wire 2 of the top leading end portion 10 gradually changes through stepped portions (S) so that the core wire 2 progressively reduces its thickness (T1, T2) stepwise while successively increasing its breadth (B1, B2) stepwise approaching a foremost distal end of the top leading end portion 10.

The flat plane structure 13 is such that the helical coil body 3 and the core wire 2 are subjected to a bending, twisting and turning operation by manipulating the hand access portion (not shown). The stepped portions (S) are provided with the core wire 2 as stress concentration points in which the stepped portions (S) dominate flexibility, twistability, torque transmissibility and sensitivity against the top leading end portion 10 when the top leading end portion 10 is subjected to an exterior force. Due to the gradually changing structure in which the top leading end portion 10 is formed to be thinner and wider stepwise toward its distal extreme end with the stepped portions (S) as nodal points, more improved mechanical properties are provided with the top leading end portion 10 of the flat plane structure 13.

Such is the top leading end portion 10 that the core wire 2 is formed to be thinner and wider stepwise toward its distal end portion with the stepped portions (S) as nodal points in the flat plane structure 13. The core wire 2 dominates the bending characteristics of the top leading end portion 10 when the top leading end portion 10 is subjected to a torsional force (rotational force) upon manipulating the hand access portion or when subjected to a bending force as a reaction upon inserting it into the blood vessel.

For this reason, the stepped portions (S) are subjected to concentrated stresses with segment plates 2a, 2b, 2c as bending sections when subjected to the torsional and bending displacements.

The segment plates 2a, 2b, 2c divided by the nodal points are subjected to the bending and torsional forces at once depending on a flattened degree of the respective segment plates 2a, 2b, 2c so as to make the resultant force work on the top leading end portion 10 as a whole. Due to the resultant force, the segment plate 2a between the first stepped portion (S) and the foremost distal end of the core wire 2 serves as a short tongue piece conducive to providing it with a good flexibility and tactility due to sensitivity against the vascular wall and the diseased area.

Figure 3:
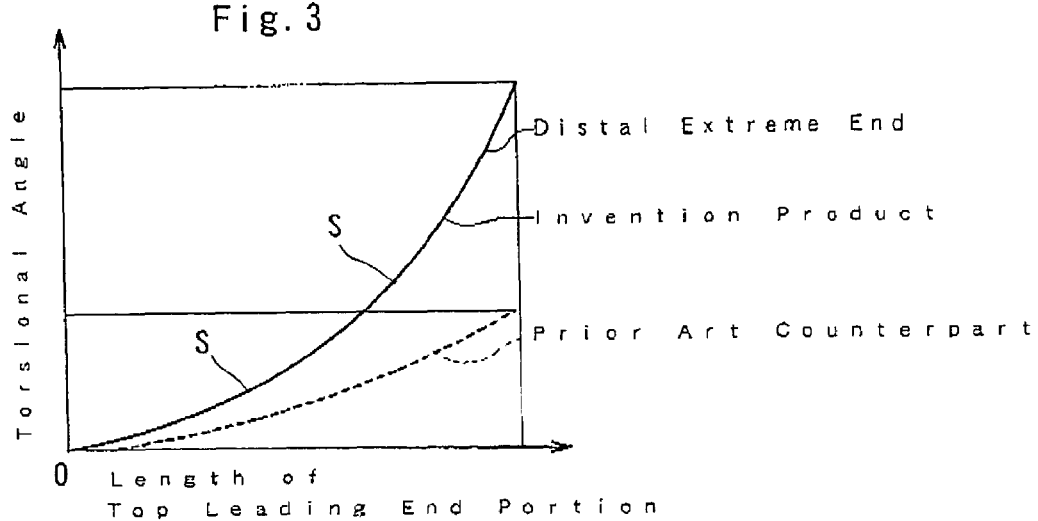
FIGS. 3 and 4 are torsional curves characteristic of the top leading end portion of the medical guide wire.
Figure 4:
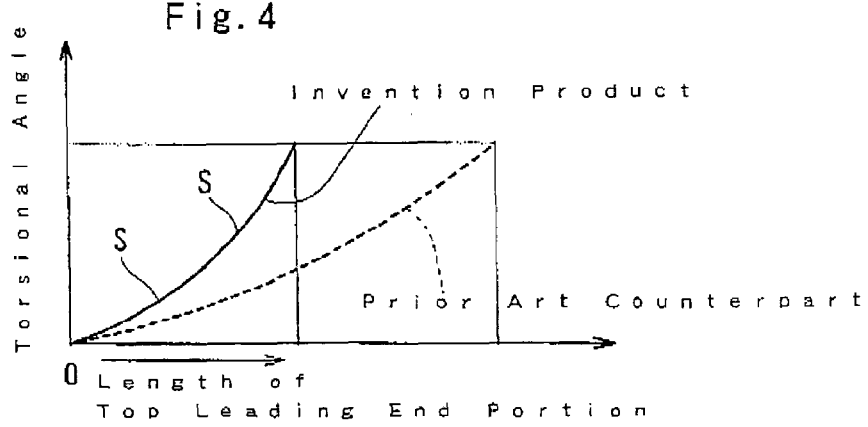
Figure 5:
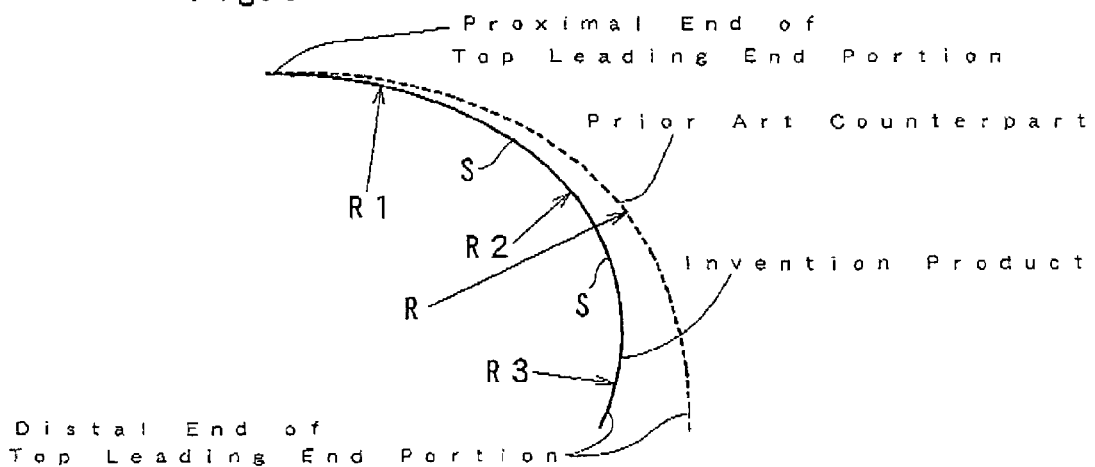
FIG. 5 is a bending curve characteristic of the top leading end portion of the medical guide wire.

Characteristics derived from the basic structure of the invention are shown in FIGS. 3, 4 and 5. Relative torsibility and bending property are compared between the present invention (referred to as "invention product" hereinafter) and the guide wire derived from the laid-open Japanese Patent Application No. 4-292175 (referred to as "prior art counterpart" hereinafter). In this instance, the length (L), breadth (B1) and thickness (T1) of a proximal end of the core wire 2 and the breadth (B2) and thickness (T2) of a distal end of the core wire 2 are identical dimensions between the invention product and the prior art counterpart. As shown at the solid line in FIG. 3, the core wire 2 of the invention product stepwise increases a torsional angle progressively as approaching its distal extreme end with the stepped portions (S) worked as the bending sections when subjected to the torsional force.

Due to the torsility which rapidly raises the torsional angle as approaching the distal extreme end, a shorter length is required for the core wire 2 to have a predetermined torsional angle when the invention product and the prior art counterpart are subjected to the same torsional force as shown at the solid line and broken lines in FIG. 4. The invention product has the torsility quickly raising the torsional angle and the torsional deformation so as to remarkably improve the torsility at the narrow segments of the front distal end portion 6.

When the top leading end portion 10 is subjected to the bending force, contrary to the prior art counterpart which deforms substantially with a uniform radius of curvature (R) as shown at the broken lines in FIG. 5, the core wire 2 of the invention product deforms with radii of curvature (R1), (R2) and (R3) progressively decreasing from the distal end to the proximal end of the top leading end portion due to the bending rigidity (expressed by inertia moment×Young's modulus) of the segment plates 2a, 2b, 2c divided by the stepped portions (S). This remarkably increases a total bending deformation of the core wire 2 compared to that of the prior art counterpart under the same bending force so as to impart the narrow segments of the front distal end portion 6 with a high flexibility. The first segment plate 2c of the segment plates 2a, 2b, 2c works as an independent tongue piece to exhibit a sensitivity and a good detection ability against the vascular wall and the diseased area.

Figure 12:
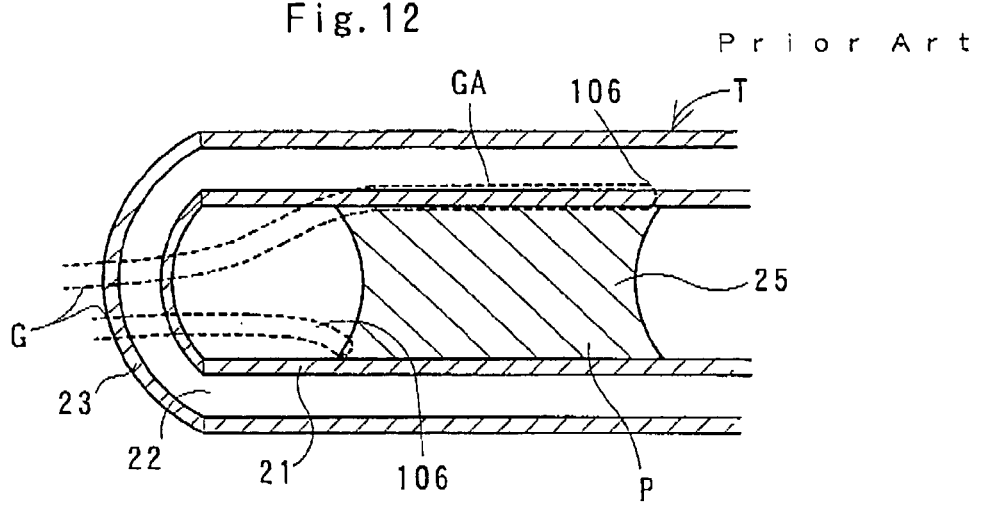
FIGS. 12, 13 and 14 are explanatory views showing how the medical guide wire works.
Figure 13:
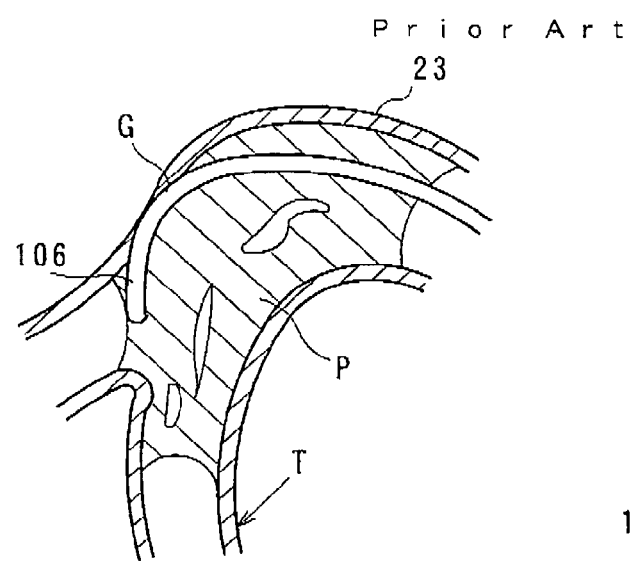
Figure 14:
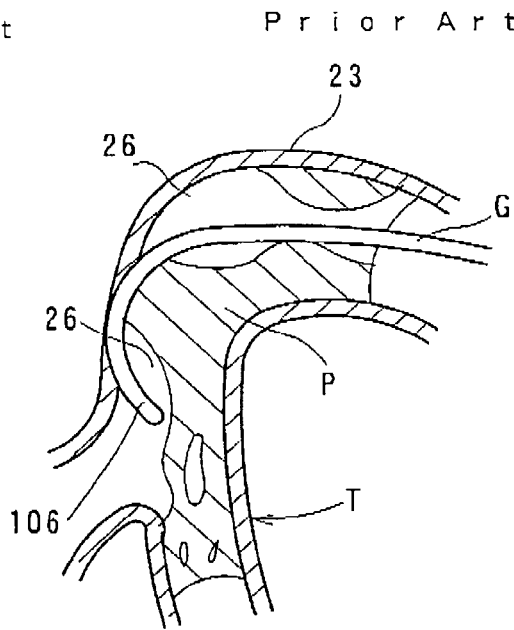
Figure 15:
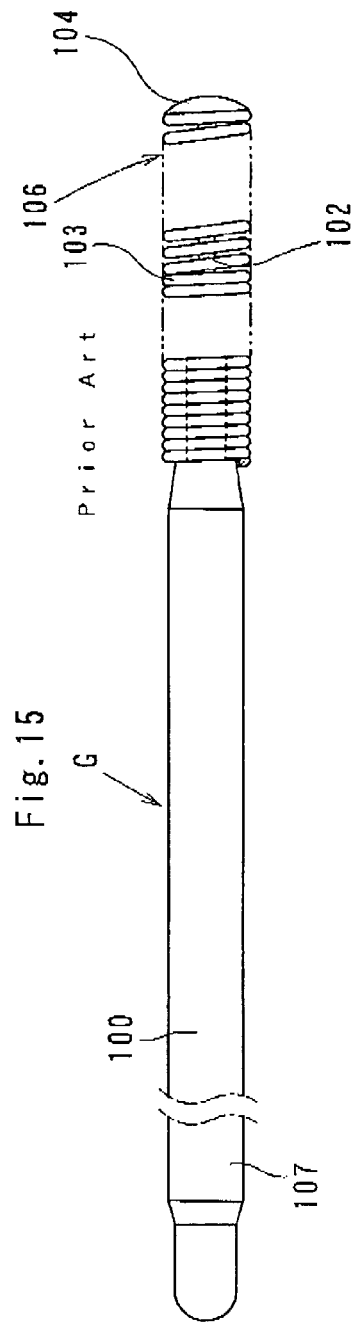
FIG. 15 is a plan view of a prior art medical guide wire.
Figure 16:
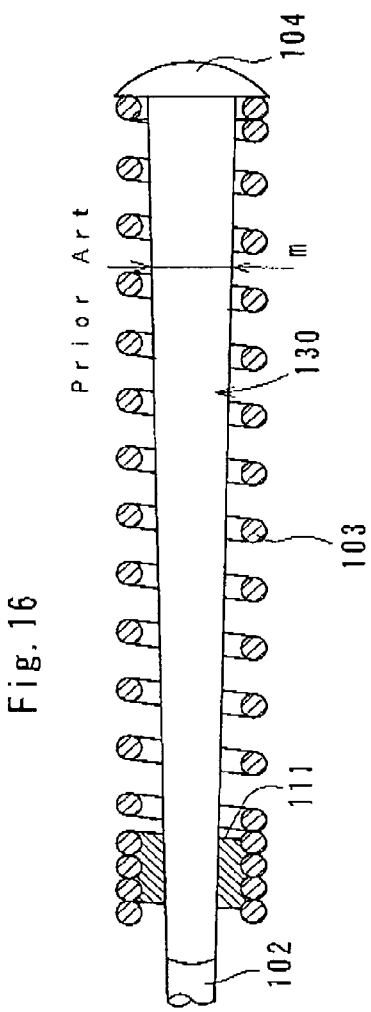
FIG. 16 is a longitudinal cross sectional view of the prior art medical guide wire.
Figure 17:
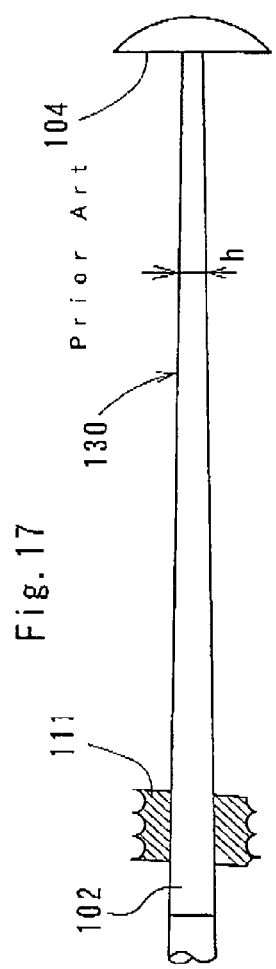
FIG. 17 is a plan view of the prior art medical guide wire; but a helical coil body is removed.

Based on the high flexibility, the sensitivity and the tongue piece touch, it is possible to provide the foremost distal end of the top leading end portion 10 with the detection ability against the vascular stenosis and the obstructed area of the blood vessel, while at the same time, ensuring an ablative ability against a tiny portion of the diseased area owing to a sensitivity against the vascular wall and the diseased area. For these reasons, it is possible to prevent the top leading end portion 10 inducing the false lumen 26 and to prevent it from advancing into the adventitia 23 as opposed to the prior art counterpart as shown in FIGS. 12-14.

It is to be noted that the good bending characteristics are not hindered by providing an annular space between the stepped portions (S) and the helical coil beady 3. On the contrary, in a guide wire structure in which the core wire is coated with a synthetic resin layer, the bending characteristics decline depending on coating conditions of the synthetic resin layer.

According to the invention, when the manipulator advances the foremost distal end of the top leading end portion 10 to encounter the vascular wall and the diseased area, the manipulator stands to gain the torsional feeling, the sensitivity, the bending resistance and the tongue piece touch based on the twistability of the top leading end portion 10. This enables the manipulator to precisely sense the shape of the vascular wall and the shape of the diseased area so as to efficiently steer the guide wire 1 with a smooth maneuverability.

The top leading end portion 10 has the core wire 2 firmly secured to the helical coil body 3 in one piece, and the top leading end portion 10 rotates in unison with the core wire 2 and the helical coil body 3 so as to act as a penetrating drill. This imparts the top leading end portion 10 with an enhanced penetrating power and a propelling power as compared to a distal end structure in which the core line securement portion 11 is not provided.

Even under the condition that the wire element of the helical coil body 3 is 0.070-0.090 mm in diameter and its tensile strength is not great, the core line securement portion 11 prevents application of an excessive load to the helical coil body 3, thus preventing breakage of the helical coil body 3 due to an irregular lead pitch deformation induced under an excessive torsional force.

The core line securement portion 11 also prevents the helical coil body 3 from being wavily deformed so as to ensure the top leading end portion 10 with a good penetrating power against the diseased area and a good insertability against the blood vessel.

It is possible to adequately adjust a ratio (T1/T2) of the thickness (T1, T2) and a ratio (B1/B2) of the breadth (B1, B2) of the segment plates 2a, 2b, 2c divided by the stepped portions (S). With this in mind, a level-reducing amount of the stepped portions (S) can be appropriately adjusted.

By adjusting a rigidity determinant factor like an inertia moment calculated with a center of the thickness of the segment plates 2a, 2b, 2c as a neutral plane, it is possible to ensure a balance between an optimal flexibility and a vertical load applied to the top leading end portion 10. When providing the flexibility with the top leading end portion 10 as pliable as that of the duckbill structure derived from the prior art counterpart, it is possible to cope with the vertical load applied to the top leading end portion 10 by increasing the thickness of the segment plates 2a, 2b, 2c of the flat plane structure 13. The duckbill structure of the prior art counterpart has a maximum breadth in the proximity of the head plug, while the invention product has a uniform breadth at each of the segment plates 2a, 2b, 2c. It is possible to determine the top leading end portion 10 to be diametrically smaller by reducing a maximum breadth of the segment plate 2c. With the top leading end portion 10 diametrically reduced, it is possible to further improve the insertability against smaller blood vessels of the heart and the liver.

Under the presence of the stepped portions (S), it is possible to easily and stably preshape the top leading end portion 10 with the stepped portions (S) as the bending sections before inserting it into the blood vessel. This is because it is necessary to get the top leading end portion 10 plastically deformed slightly in advance with a fingertip so as to enable selective insertion at the bifurcated portion of the blood vessel.

FIGS. 6 and 7 show a second embodiment of the invention. In FIGS. 6 and 7, the front distal end structure of the guide wire is depicted for a cardiovascular treatment. In the top leading end portion 10 of the flat plane structure 13, a core wire portion 14 circular in cross section is provided in a fashion to protrude somewhat lengthwisely from the core line securement portion 11. The core wire portion 14 is contiguous with the flat plane structure 13 in which the core wire 2 has three stepped portions (S) provided at boundaries of the segment plates 13A, 13B, 13C.

In this instance, the top leading end portion 10 measures 24 mm in length (L) from the core line securement portion 11 to a top distal end of the head plug 4. The core wire portion 14 measures 0.055 mm in diameter. The core wire portion 14 measures 3.0 mm in length which protrudes from core line securement portion 11.

As regards the flat plane structure 13, the third segment plate 13C measures 5.0 mm in length, 0.048 mm in thickness and 0.0494 mm in breadth. The second segment plate 13B measures 5.0 mm in length, 0.035 mm in thickness and 0.0678 mm in breadth. The first segment plate 13A measures 11.0 mm in length from the stepped portion (S) to the top distal end of the head plug 4. The first segment plate 13A further measures 0.028 mm in thickness (T) and 0.0848 mm in breadth (B). The breadth of the segment plates 13A, 13B, 13C are calculated based on their thickness on the assumption that each cross sectional area of the segment plates 13A, 13B, 13C is equal.

FIGS. 8 and 9 show a third embodiment of the invention. In FIGS. 8 and 9, the front distal end structure of the guide wire is depicted for a liver treatment. In the top leading end portion 10 of the flat plane structure 13, the guide wire is depicted for a liver treatment. In the top leading end portion 10 of the flat plane structure 13, the core wire portion 14 is tapered off toward the segment plates 13A, 13B, 13C. The top leading end portion 10 measures 45 mm in length (L) from the core line securement portion 11 to a top distal end of the head plug 4. Three stepped portions (S) are provided at boundaries of the segment plates 13A, 13B, 13C in the same manner as described in the second embodiment of the invention.

The core wire portion 14 measures 24 mm in length and 0.112 mm in diameter at a proximal end of the core line securement portion 11. The core wire portion 14 measures 0.063 mm in diameter at its top distal end which has a straight linear portion 14A protruded by 2.0 mm in length.

As regards the flat plane structure 13, the third segment plate 13C measures 5.0 mm in length, 0.06 mm in thickness and 0.0591 mm in breadth. The second segment plate 13B measures 5.0 mm in length, 0.05 mm in thickness and 0.0623 mm in breadth. The first segment plate 13A measures 9.0 mm in length from the stepped portion (S) to the top distal end of the head plug 4. The first segment plate 13A further measures 0.04 mm in thickness (T) and 0.0778 mm in breadth (B). The breadth of the segment plates 13A, 13B, 13C are calculated in the same manner as described in the second embodiment of the invention.

Figure 10:
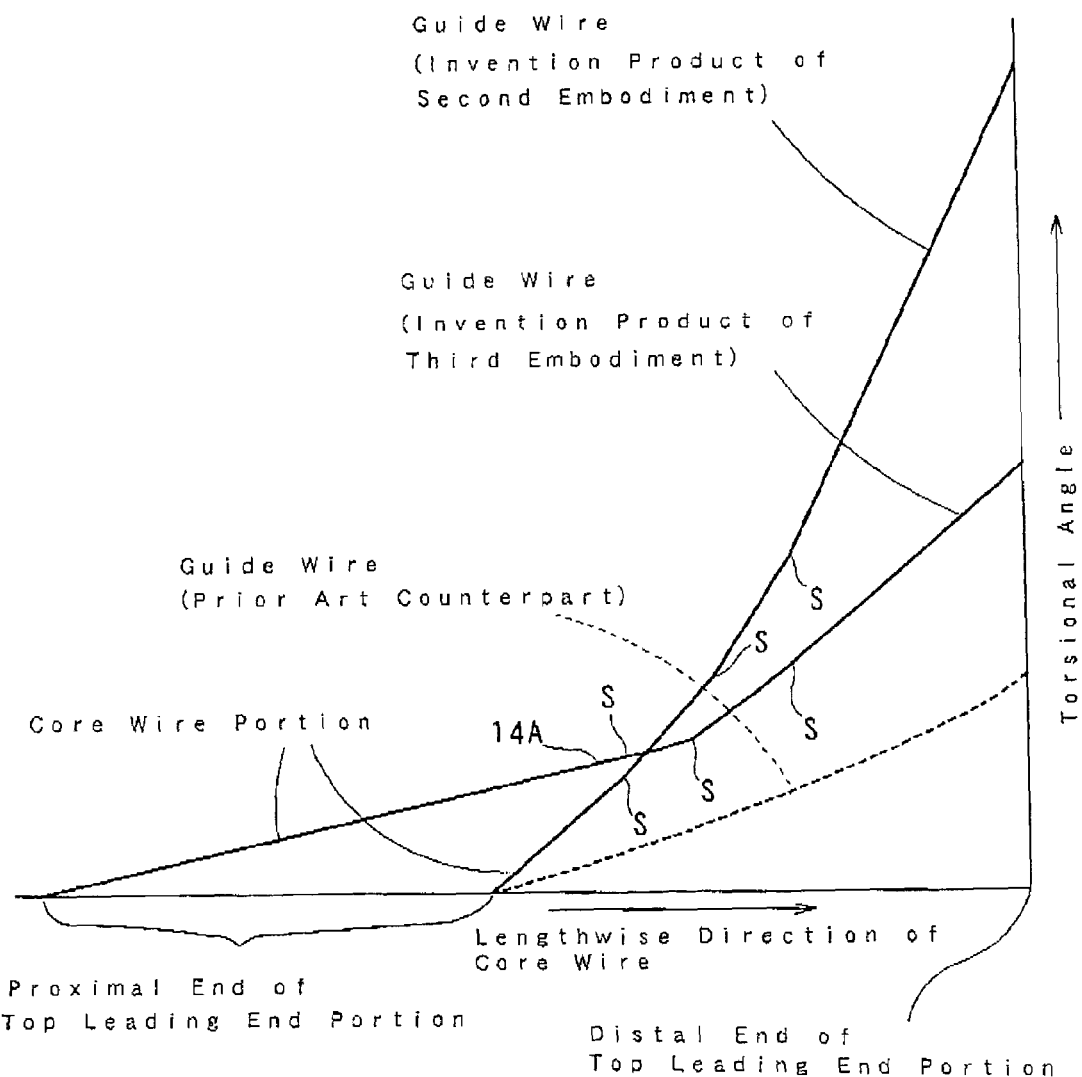
FIG. 10 shows comparative curves in terms of torsional characteristics.

FIG. 10 shows a torsional flexibility expressed in terms of a torsional angle as a relative characteristic among the invention product and the prior art counterpart. From a graphical representation of FIG. 10, it is understood that the core wire 2 exhibits a remarkable flexibility in the proximity of the head plug 4 compared to the prior art counterpart when subjected to the bending force and the torsional force.

Under the presence of the core wire portion 14 having a greater rigidity between the core line securement portion 11 and the flat plane structure 13 as shown in FIGS. 8 and 9, it is possible to ensure a proximal portion of top leading end portion 10 with a good torsional rigidity so as to enhance the torque transmissibility. Further, the flat plane structure 13 enables the guide wire to a greater torsional angle at its narrow section to impart a remarkable flexibility in the proximity of the head plug 4 so as to favorably improve the cardiovascular treatment procedure. This is all the more true because the top leading end portion 10 is compatible to dimensions of the cardiovascular system and diseased area in terms of the length (L).

The reasons why the length (L) of the top leading end portion 10 measures 24 mm in the second embodiment of the invention are as follows:

The obstructed area of the cardiovascular system generally extends often by 10-15 mm. In order to prevent the core line securement portion 11 from getting stuck in the diseased area, it is preferable that the top leading end portion 10 extends beyond 10-15 mm with its bending configuration taken into consideration, and thus improving the insertability against the obstructed area of the cardiovascular system.

In the third embodiment of the invention, the core wire portion 14 is tapered off toward the segment plates 13A, 13B, 13C so that the core wire portion 14 progressively reduces its torsional rigidity toward the segment plates 13A, 13B, 13C. This helps make the manipulation smooth with the top leading end portion 10 highly rendered flexible from the proximal end to the distal end thereof.

The reason why the top leading end portion 10 measures 45 mm in length (L) is that the size is compatible to the hepatovascular treatment so as to improve its treatment procedure. This is all the more true since the hepatovascular system is complicated at its tortuous path, in addition to the fact that the purpose of using the guide wire is to staunch the blood stream against the carcinogenic lesion.

Figure 11:
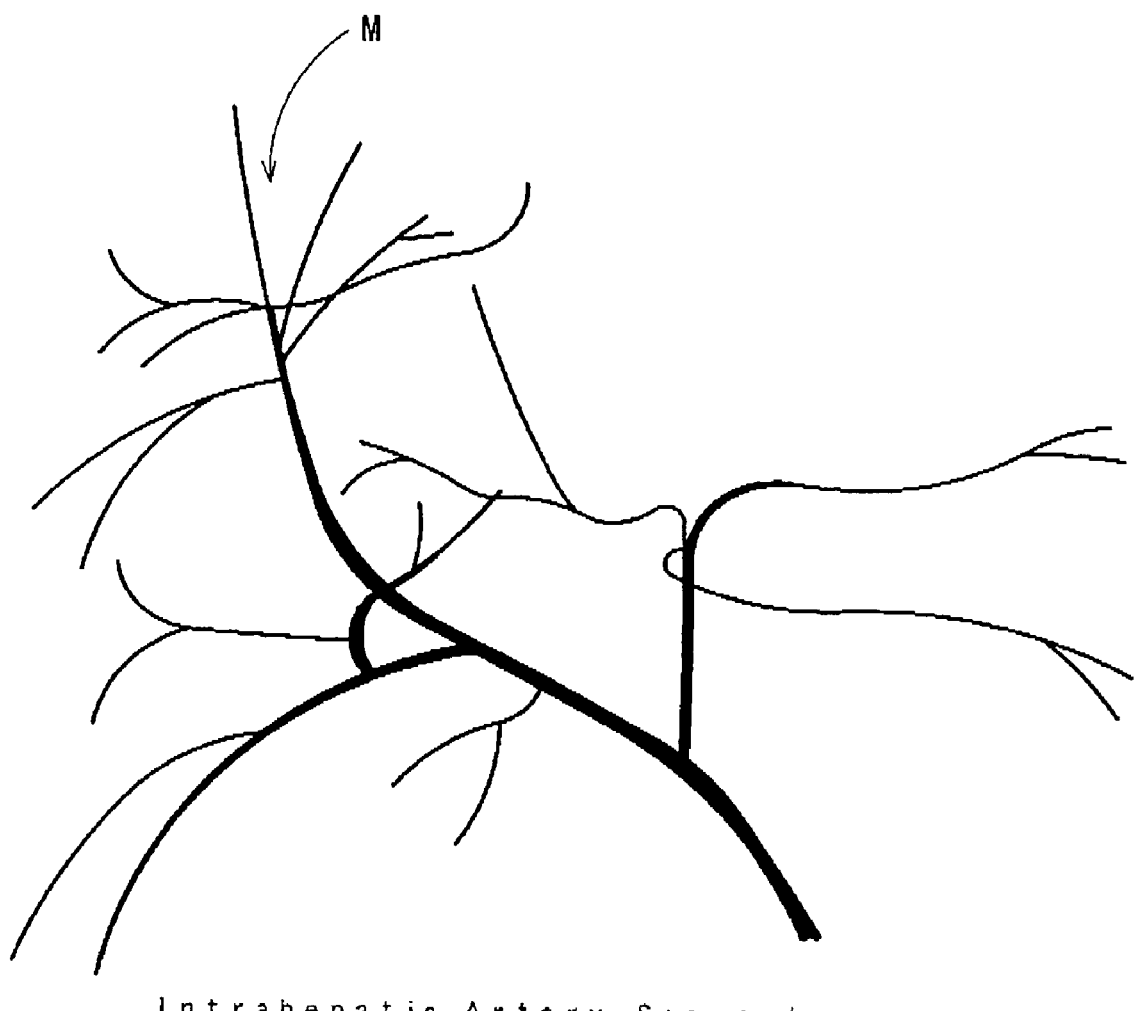
FIG. 11 shows a schematic view of intrahepatic artery segments.

In particular, the purpose of the hepatovasoular treatment is to staunch the blood stream against the carcinogenic lesion (hepatovascular TAE) among the small and meandering blood vessel. In order to steer the guide wire deeply without getting the core line securement portion 11 stuck in the peripheral blood vessel, it is preferable to locate the core line securement portion 11 just before the bifurcated portion of the small blood vessel (e.g., right hepatovascular artery) while placing the head plug 4 at the diseased area of the peripheral section of the bifurcated portion of the small blood vessel (e.g., upper front segmental branch M in FIG. 11).

For this reason, the length (L) of 24 mm is preferable to get the guide wire locate in the advantageous position with a good insertability ensured.

Upon steering the guide wire through the blood vessel, the top leading portion 10 is subjected to considerable torsional deformation and bending deformation with the stepped portions (s) as the stress concentration sections. Since the guide is used only once with one operation, the guide wire including the stress concentration sections is not subjected to harmful deformation or breaking.

As a fourth embodiment of the invention, the core wire 2 is made of stranded wires, an outer surface of which is diametrically reduced by means of a diameter-reducing procedure (e.g., swaging dies).

With the core wire 2 made of the stranded wires, it is possible to impart the top leading end portion 10 with an increased flexibility so as to protect it against bending due to repeated insertion procedures against the tortuous blood vessel.

With the core wire 2 diametrically reduced throughout its entire length, it is possible to increase the rigidity so as to effectively protect the core wire against the bending tendency. With parts of the core wire 2 diametrically reduced throughout its specified lengths, it is possible to provide a gradient property with the core wine 2 flexible in one part and rigid in other part.

The core wire 2 is made of the austenitic stainless steel in the fifth embodiment of the invention. With the core wire 2 made of the austenitic stainless steel, the core wire 2 is unlikely to be broken easily even under the influence of the soldering or brazing procedure when the head plug 4 and the core line securement portion 11 are secured to the core wire 2, as opposed to the martensitic stainless steel and the ferritic stainless steel which exhibit the quench-hardening and high temperature fragile properties.

With the austenitic stainless steel higher in electrical resistance than any other stainless steels, it is possible to minimize the heat production due to the welding procedure, thus mitigating an unfavorable bending deformation of the core wire 2 under the influence of the heat of the welding procedure.

The work-hardening nature of the diameter-reducing procedure facilitates multiple types of reshaped and preshaped configurations of the core wire depending on the conditions of the diseased area to be cured.

With the use of a shape-memory alloy (e.g., nickel-titanium alloy), it is possible to eliminate the necessity of preparing several types of core wires depending on the conditions of the diseased area to be cured.

It is to be noted that only one stepped portion (S) may be provided in the proximity of the front distal end portion 6 of the core wire 2 because it is sufficient as long as the top distal end of the core wire 2 maintains the tongue piece function. The core wire 2 of the flat plane structure 13 may progressively decrease its cross sectional area toward its top distal end portion. The stepped portions (S) may be provided with the duckbill structure. Further, the stepped portions (S) may have a curved surface at a stepped portion so as to mitigate the stress concentration.

What is claimed is:

1. A medical guide wire having a stepwisely thickness-reduced but breadth-increased distal tip structure comprising:
    a core wire inserted into a helical coil body;
    a head plug attached to a distal end of said core wire and a distal end of said helical coil body;
    a core line securement portion in which said core wire is firmly fixed together in one piece to an inner side of said helical coil body so as to form a top leading end portion between said core line securement portion and said head plug; and
    a flat plane structure having corresponding segment plates in which said core wire of said top leading end portion gradually changes through a plurality of stepped portions that act as transitions between said segment plates within said helical coil body so that the thickness of said core wire is progressively reduced stepwisely while the breadth of said core wire is successively increased stepwisely as approaching a foremost distal end of said top leading end portion, wherein
        said core wire of said top leading end portion has a core wire portion circular in cross section so that said segment plates of said flat plane structure extend contiguously forward from said core wire portion;
        the core wire has a constant cross-sectional area throughout the segment plates along a lengthwise direction of said core wire; and
        a respective thickness of each segment plate of the core wire is constant between adjacent stepped portions along the lengthwise direction of said core wire.

2. The medical guide wire having a stepwisely thickness-reduced but breadth-increased distal tip structure according to claim 1, wherein said core wire portion of said top leading end portion is tapered off toward a foremost distal end of said top leading end portion.

3. The medical guide wire having a stepwisely thickness-reduced but breadth-increased distal tip structure according to claim 1 or 2, wherein the number of said stepped portions of said flat plane structure is two or three.

4. The medical guide wire according to claim 3, wherein said core wire is made of an austenitic stainless steel.

5. The medical guidewire having a stepwisely thickness-reduced but breadth-increased distal tip structure according to claim 1 or 2, wherein said top leading end portion measures 24 mm in length for use in coronary heart treatment.

6. The medical guide wire having a stepwisely thickness-reduced but breadth-increased distal tip structure according to claim 1 or 2, wherein said top leading end portion measures 45 mm in length for use in hepatovascular treatment.

7. The medical guide wire according to claim 1, wherein said top leading end portion has a dimensional length of 24-45 mm measured from a foremost distal end of said plug head to said core line securement portion.

8. The medical guide wire according to claim 1, wherein said core wire is in the form of stranded wires.

9. The medical guide wire according to claim 8, wherein said core wire is wrought to reduce the outer diameter of said core wire by means of a diameter-reducing treatment.

10. The medical guide wire according to any of claims 1, 2, and 7-9, wherein said core wire is made of an austenitic stainless steel.

* * * * *